United States Patent [19]
Faulhaber et al.

[11] 4,005,281
[45] Jan. 25, 1977

[54] DEFECT IDENTIFICATION WITH NORMALIZING OF GAIN FUNCTION IN OPTICAL-ELECTRICAL INSPECTION

[75] Inventors: Mark Edwin Faulhaber; Edmund Haislett Smith, Jr., both of Wilmington, Del.

[73] Assignee: E. I. Du Pont de Nemours and Company, Wilmington, Del.

[22] Filed: May 14, 1975

[21] Appl. No.: 577,394

[52] U.S. Cl. .............................. 235/151.3; 356/239
[51] Int. Cl.² ......................................... G06F 15/00
[58] Field of Search ....................... 235/151.3, 152; 178/7.1, 6, DIG. 34, 33, 28; 356/239, 237, 199, 200; 328/151

[56] References Cited
UNITED STATES PATENTS

| | | | |
|---|---|---|---|
| 3,557,354 | 1/1971 | Trimble | 235/152 |
| 3,800,078 | 3/1974 | Cochran et al. | 178/7.1 |
| 3,843,890 | 10/1974 | Anthony, Jr. | 356/239 X |

Primary Examiner—Edward J. Wise

[57] ABSTRACT

Method and apparatus for defect identification with normalizing of the optical-electrical inspection system gain function of scans across a full width of running product web in order to facilitate defect amplitude discrimination within the uneven portions of repetitive scan signals, and then, after accumulating a preselected number of gain-normalized scans, identifying protracted duration defect-related signals by amplitude discrimination.

12 Claims, 6 Drawing Figures

DEFECT IDENTIFICATION WITH NORMALIZING OF GAIN FUNCTION IN OPTICAL-ELECTRICAL INSPECTION

BRIEF SUMMARY OF THE INVENTION

Generally, this invention comprises a method and apparatus for defect identification with normalizing of the optical-electrical system gain function of scans across a full width of running product web comprising (1) storing an accumulation of characteristic individual electrical recurring scan signals A and dividing the accumulation by the number of signals A stored to obtain a stored reference signal R, (2) differencing each succeeding scan signal A with the stored reference signal R to obtain a zero-based difference signal, thereby equalizing each successive scan signal A while preserving defect-related signals and (3) identifying the defect-related signals by amplitude discrimination of the zero-based difference signal.

The identification of subtle protracted duration machine direction defects, such as streaks in photographic film, is further facilitated by subjecting the difference signals derived from step (2) supra to coherent adding over a plurality of scans in order to relatively enlarge the magnitude of defect-related signals prior to their identification.

GENERAL BACKGROUND

In order to discriminate either isolated defects or streaks in product webs, an inspection system should first have constant sensitivity to defect conditions which may be encountered at any point in a full scan across the web. Methods of compensating for scan-to-scan sensitivity variations have hitherto assumed that the optical and electrical efficiencies of the scanning system remain constant over each scan length. However, in order to meet high precision inspection requirements, these assumptions do not apply and it is necessary to use a system that corrects for variations in optical/electrical efficiencies throughout each product scan (i.e., across the normally generated scan signal).

This invention is applicable to repetitive scan signals generally, particularly where the magnitudes of signal variation are not large; however, it is equally applicable to pedestal signals displaying relatively large signal variations, in which case logarithmic processing of the scan signals before input to the apparatus of this invention is advantageous.

Optical-electrical photographic film inspection generates non-flat pedestal signals, the compensating of which, according to this invention, requires two operations: (1) storing a logarithmically processed characteristic irregular pedestal reference signal R in a first digital memory circuit and (2) differencing each new log-processed scan A with the stored reference signal to derive the requisite log ratio result, log A/R. The equalized (flattened) instantaneous difference log ratio signal thereby obtained effectively places in true perspective the amplitudes of defect-related signals previously buried in the uneven repetitive portions of the pedestal and thereby facilitates their detection by bipolar amplitude discrimination means.

As a further operation, streak detection is achieved by subsequently accumulating the sums of the amplitudes of the instantaneous difference signals over several scans in a second memory. This procedure is defined as "coherent adding". Summing these difference signals limits the build-up of uncorrelated noise appearing on the pedestals, whereas persistent signal level shifts, such as caused by machine direction streaks, will accumulate rapidly. The second memory is reset automatically when the sum includes a sufficient number of scans to effect a good time average of the difference signals.

An alternate scheme may be used to accumulate the instantaneous difference signals when low frequency machine direction level shifts occur as a result of the product web passing over off-center rolls or from other causes, such as web flutter, which might otherwise be detected as defective product. In these situations, a digital differentiation scheme, effected by inverting and summing the alternate scan instantaneous difference signals with the address shifted accumulated partial sum values of the instantaneous difference signal waveforms stored in the second memory effectively nullifies the accumulation of these periodic bias level changes.

In general, the complete equalizer and streak detection apparatus of this invention for photographic film inspection comprises an A/D converter, two random access memories, two D/A converters and various digital control and arithmetic circuitry arranged in two adjoining loops. Each loop is provided with a random access memory and an adder-subtractor, and functions independently of the other in two operating modes.

The first mode establishes a mean pedestal waveform obtained by averaging the amplitude samples within each sampling interval of each scan in a series of $2^n$ scans over a streak-free product. The elements in the first loop function first to accumulate a sum of the sampled amplitude values over the predetermined sequence of scans, then to derive, by means of a shifter, the average value of each sample by shifting each of the accumulated binary values stored in the first random access memory a predetermined n places in a known manner and finally to initiate the second operating mode. Although the stored standard waveform amplitude values can be maintained indefinitely in memory, for varying product roll conditions it has been found desirable to compute and store a new reference for each product run (or for each product roll).

The second mode first obtains the differences between the sampled amplitude values of the mean pedestal waveform developed in the first mode and the corresponding sample values of the instant product scan and then accumulates these instantaneous difference signals in one of two selectable ways in the second loop random access memory for later discrimination. In this manner, where, on the one hand, uncorrelated product noise will be summed to zero over the series of P product scans (where P = number of scans accumulated in the second loop before resetting), on the other, machine direction streaks having correlated signal amplitude values will rapidly build in value for easy defect discrimination. The rate at which the defect signal accumulates in memory is dependent on the severity, persistence and orientation of the streak with respect to the machine direction. Reset of the second random access memory occurs automatically when a sufficiently long time average has been obtained, e.g., on the order of P = 300 scans.

A variation of the straight additive accumulation scheme that is useful when low frequency machine direction noise is present includes inverting the instantaneous difference signals and shifting the address locations of the stored partial sum values in the second memory on the even (or odd) scans. This is equivalent to digital differentiation, since small constant changes in signal level are essentially nullified, whereas subtle streak amplitudes are allowed to build up, but at half the rate of the straight additive accumulation procedure hereinbefore described.

DRAWINGS

The following drawings constitute part of this specification, in which.

Figure 1:
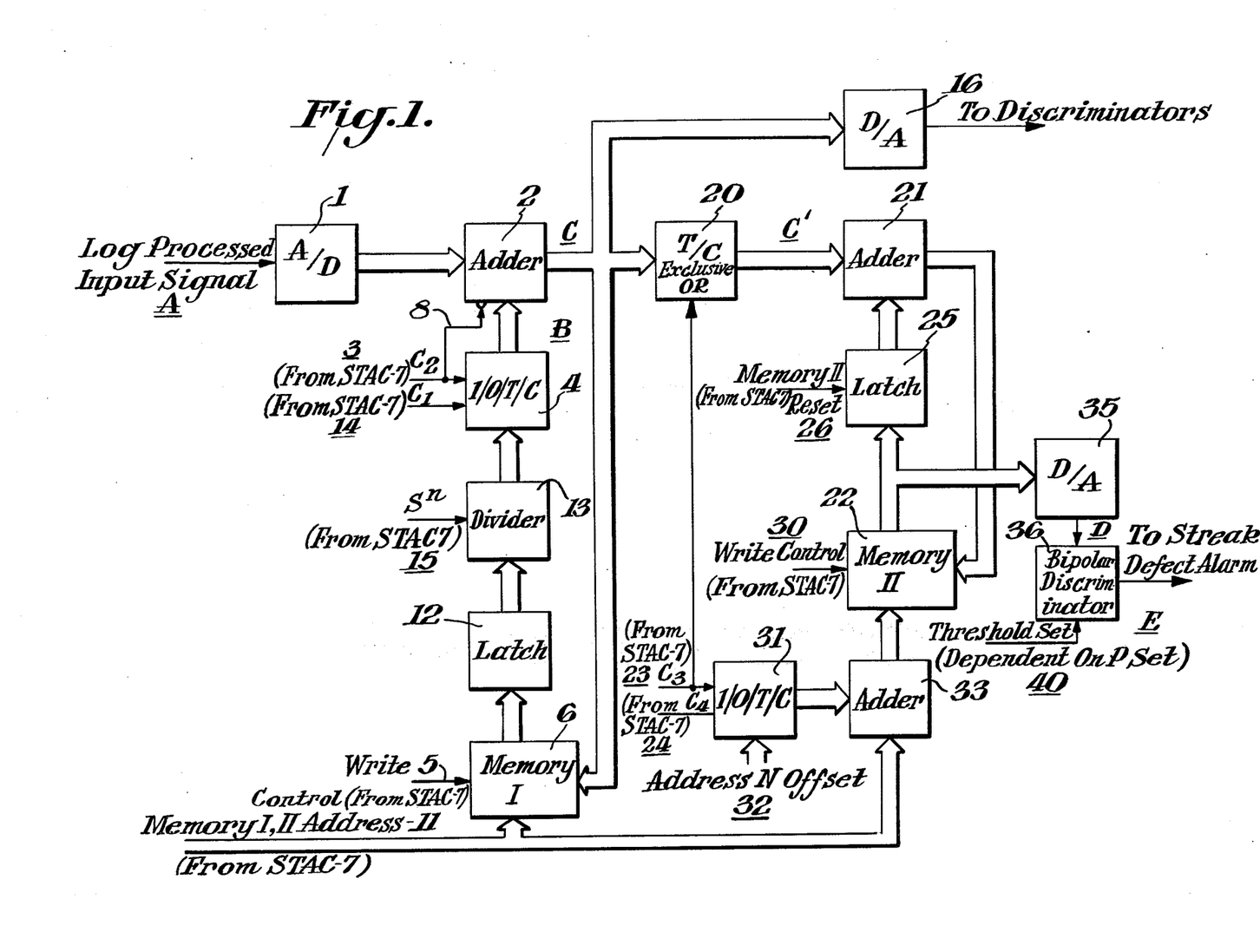
FIG. 1 is a block diagram of the pedestal equalizer and streak detection system.

Referring to FIG. 1, and analog log-processed input signal A is applied to the input terminal of the A-D converter 1, typically an I.C.E. Model IAD 1310M having output terminals connected to a first set of input terminals of adder 2. Adder 2, which is the first of five elements forming the first loop, is typically a SN7483, and functions to add each amplitude sample of binary converted input waveform A to the binary value of the corresponding digital unit sampling interval appearing at its second set of input terminals, which are connected to the output terminals of ONE/ZERO/TRUE/-COMPLEMENT (1/0/T/C) element 4. 1/0/T/C element 4, typically a SN74H87, exercises control over the entire loop on command from signals $C_1$, $C_2$, 14 and 3, respectively. These signals are generated by the system timing and addressing circuit (STAC) 7, FIG. 1A, and are applied to the control terminals of 1/0/T/C element 4 as shown. The system timing and addressing circuit (STAC) 7 is a conventional logic and gating circuit such as that shown in Inter-Computer Electronics, Inc. drawings Nos. 4020077 and 4020085 (two sheets). A separate line 8 is shown connecting the $C_2$ terminal of 1/0/T/C element 4 to adder 2 to provide for the 2's complement form result when one's complement binary inverted and non-inverted values are summed to produce instantaneous difference signals for input into the second loop during the mode 2 operation.

Attached to the output terminals of adder 2 are the input terminals of memory I, 6 which is the key circuit element in the first loop. During mode 1, write control command 5 enables memory I, 6 so that it repetitively stores the new partial sum value of each sampling interval received from adder 2 in the corresponding memory locations specified by addressing signal 11. However, during mode 2, write command 5 is not present and the contents of memory I remains unchanged.

Memory I, 6 of this invention is typically a semiconductor type having a 16 bit 256 channel input data capability and capacity which can handle 9 bit data words accumulated over 128 scans. However, any memory can be used which has sufficient speed and capacity to accumulate a sufficiently large sum of input waveforms across a sufficiently representative number of sampling intervals.

Latch 12, typically a N8202, connects memory I, 6 with divider 13 and serves to maintain the last stored value in memory I as a reference during those instances that memory content is updated.

To complete the loop, divider 13, typically a N8243, connects the output terminals of latch 12 to the input terminals of 1/0/T/C element 4. The function of divider 13 is to divide each of the stored partial sum amplitude values in each pedestal sampling interval accumulated over a series of $2^n$ scans in order to obtain a best average reference waveform. At the outset of mode 2, upon receiving a shift signal $S^n$ 15 from STAC at its control terminal, divider 13 will right justify n places where $n = \log_2$ (number of scans summed) and then invert the binary number sets appearing at its input terminals from latch 12 and pass the inverted binary quotient signal to 1/0/T/C element 4.

During mode 1 and recalibrate phases, when the $S^n$ signal 15 is not present at the control terminal, divider 13 is inactive and allows the inverted contents of memory I to pass to 1/0/T/C element 4.

The following table summarizes the control signal logic level values in relation to the flow of signal information during loop one's three phases of operation. Assume A is a small amplitude binary value of an input signal to adder 2 received from A/D converter 1, whereas M is the corresponding time period value of the contents of memory I.

| Loop Function | $C_1$ | $C_2$ | $S^n$ | Memory I Write | 1/0/T/C 4 Input | 1/0/T/C 4 Output | Adder 2 Output |
|---|---|---|---|---|---|---|---|
| Reset Memory I | 1 | 1 | 0 | 1 | $\overline{M}$ | 0 | A |
| Accumulate (Mode 1) | 0 | 1 | 0 | 1 | $\overline{M}$ | M | A+M |
| Difference (Mode 2) | 0 | 0 | 1 | 0 | $\overline{M/S^n}$ | $\overline{M/S^n}$ | $A+\overline{M/S^n}+1$ |

(NOTE: The bar notation above the several M containing terms denotes the complement of the memory I contents, which is the signal form of the divider 13 output.)

Since adder 2 output during mode 2 is in two's complement form (permitting arithmetic operations on both positive and negative number values), a summation of the instantaneous difference signal $A+\overline{M/S^n}+1$ in loop 2, hereinafter described, essentially limits signal accumlation to only the anomalous portions of the sampled waveforms about a zero volt base line, thereby facilitating bipolar discrimination.

More significantly it will be understood that this residual signal C is the value of the difference between two log processed values, which in this case is equivalent to the log of the ratio between the instant signal waveform and its best average over a series of $2^n$ scans.

It is this ratioing which effectively equalizes the gain across the extent of each uneven pedestal signal. For example, referring to FIG. 2, waveform AA shows the location and amplitude characteristics of a defect signal appearing on a typical uneven pedestal signal. If this same defect were to appear at the right end of the pedestal, system electrical noise would mask it, whereas if it were displaced leftward to the highest portion of the scan signal, its amplitude would be greatly exaggerated. Pedestal equalization, in accordance with this invention, forces the defect signal to appear in true perspective with respect to background noise, regardless of its location in the pedestal signal. Furthermore, in those cases where direct inspector amplitude discrimination of the waveform shown in AA of FIG. 2 would fail to detect a defect such as that indicated, simple bipolar amplitude discrimination schemes can now be used to detect both (+) and (−) defect types in accordance with the teaching of this invention.

We note that, in those cases where pedestal unevenness is small, the amplitude values of the reference waveform will be essentially constant across the pedestal width. Consequently, the position of a small defect in the scan will have negligible effect on the amplitude of its related signal and the need for ratioing is obviated since, for small differences, A-R approximates log A/R.

Returning now to FIG. 1, the output terminals of adder 2 not only connect to input terminals of memory I, 6 but also connect to (1) the input terminals of D-A converter 16, which functions during mode 2 to convert the binary valued instantaneous difference signal to analog form for direct simultaneous amplitude discrimination of each scan by means such as shown in USP Pat. No. 3,843,890, and (2) the input terminals of true/complement (T/C) element 20 (implemented using an array of exclusive OR gates in a known manner). T/C element 20 is used to invert the instantaneous difference signal on alternate scans upon occurrence of a $C_3$ signal 23 from STAC 7 when the differential mode for streak detection is selected.

In addition to true/complement element 20, the remaining elements in the second loop are centered around a second random access memory 22 and are comparable to those found in the first loop. Loop 2 operates to accumulate the log processed instantaneous difference signals in order to detect by conventional bipolar discrimination means the subtle machine direction streak-related signals as they build up in memory.

More particularly, the output terminals of T/C element 20 are attached to a first set of input terminals of adder 21, typically a SN7483, whose second set of input terminals attach to the output terminals of latch 25 (typically a N8202). Upon receipt of reset memory II command 26 from STAC 7, which in turn initiates loop 2's mode two operation, latch 25 functions to produce binary zeros at its output terminals to allow adder 21 to initialize memory II, 22 with the first difference signal input upon the first mode 2 scan. Reset memory II signal 26, occurs automatically after each preset sequence of P scans, but may be manually initiated as well. In addition to its reset function, latch 25 operates to buffer the on-going changes in memory II, 22 from affecting the binary information input signals to adder 21.

Memory II, 22 which has similar characteristics to memory I, 6, receives waveform amplitude samples from the output of adder 21 and stores this data on a scan-to-scan basis during each occurrence of write control signal 30 from STAC 7. The memory II write control signal 30 is active only during mode 2; consequently the output data from adder 2 during mode 1 is not recorded.

When the system operator selects the differentiating mode 34, at STAC 7, 1/0/T/C element 31, typically a SN74H87, functions on command from mode control signals $C_3$ and $C_4$, 23 and 24 respectively, to apply the value of operator selectable address N offset signal 32 on alternate scans to a first set of input terminals of adder 33, typically a SN7483.

Adder 33 then sums address N offset signal 32 with memory I, II addressing signal 11 applied to its second set of input terminals, with the result that, at the outset of each odd (or even) numbered scan, each memory II address is shifted N places to the right. The purpose of this operation is to alternately sum the shifted contents of memory II, 22 with the alternately inverted instantaneous difference signal from T/C element 20 in order to cancel out low frequency signal fluctuations, while at the same time permitting the defect portion of the signal to build-up. FIG. 1B shows the loop 2 (mode 2) sequence of events over a series of P = 4 scans in the differentiating mode when the signal consists of a very narrow protracted duration defect.

Figure 1A:
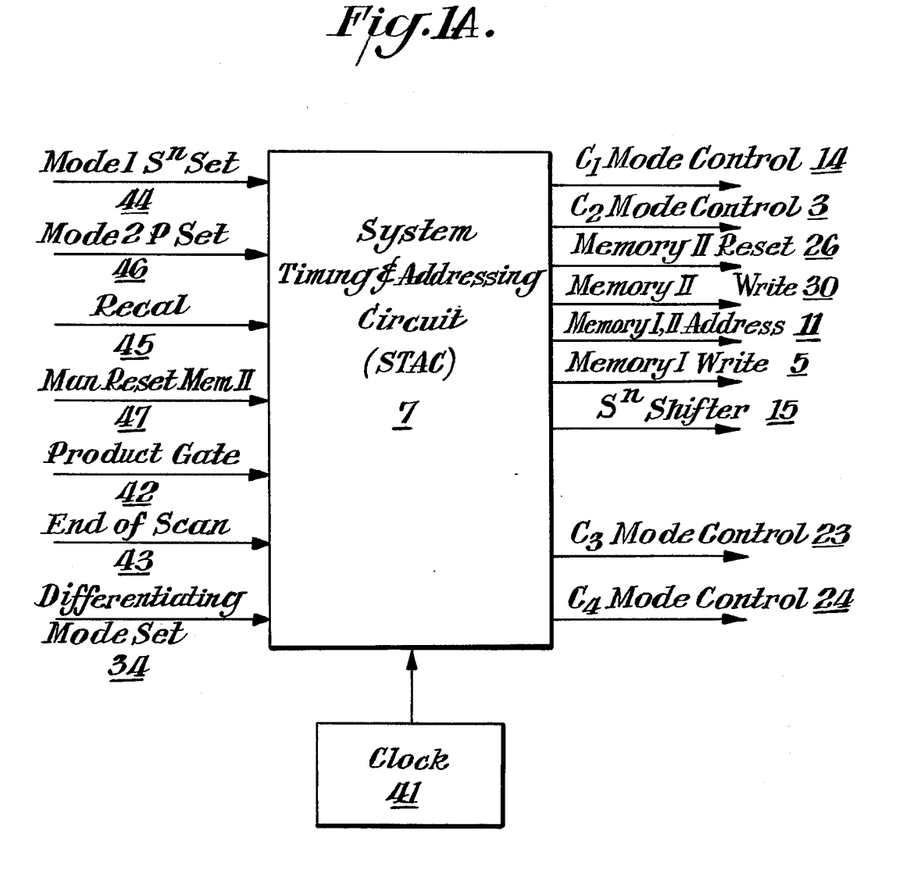
FIG. 1A is a block diagram of the system timing and addressing circuit (STAC) showing the essential input and output signals necessary to operate the system.
Figure 1B:
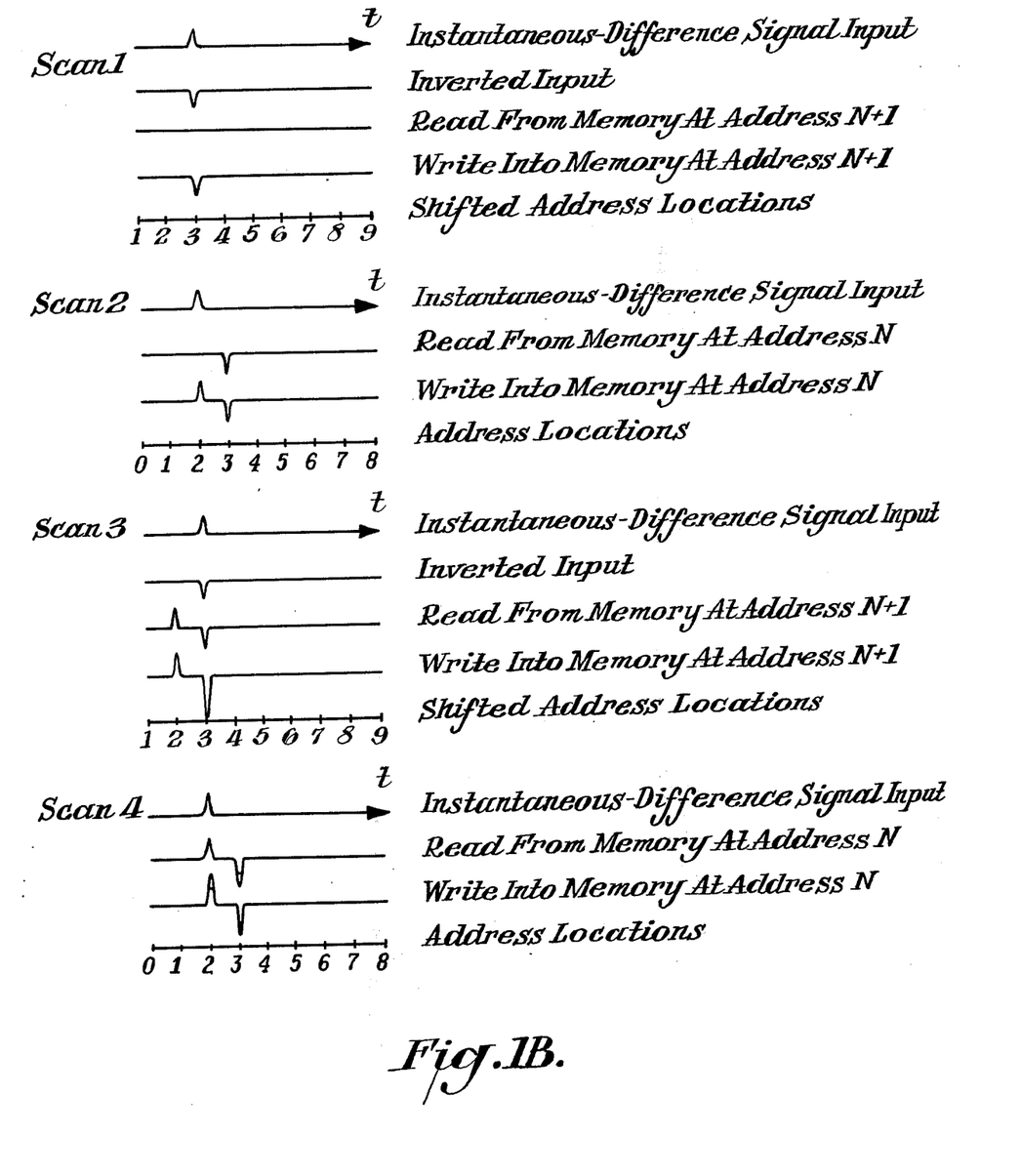
FIG. 1B is a schematic diagram showing a sequence of waveforms depicting the operation of logic elements in the differentiating mode.
Figure 1C:
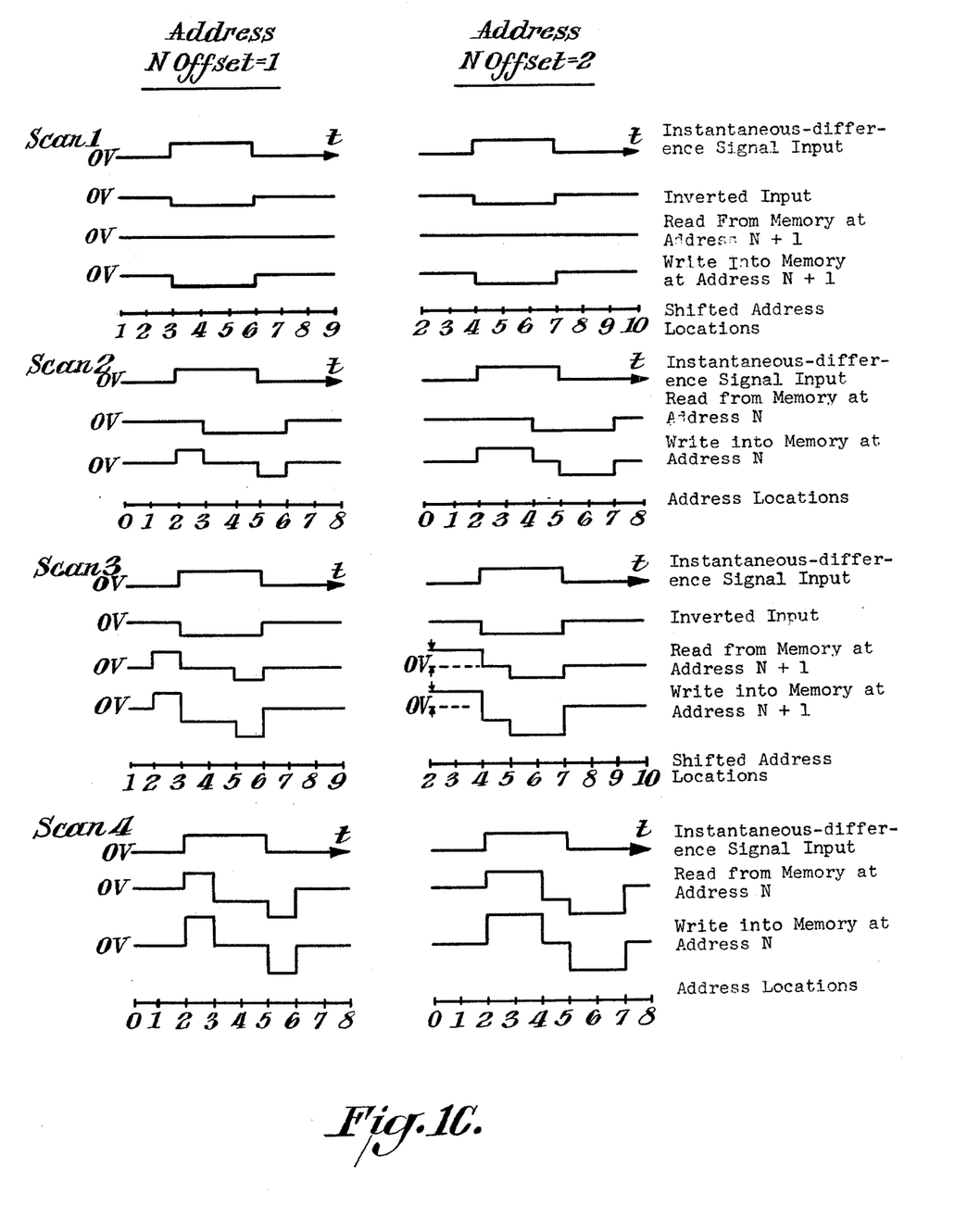
FIG. 1C is a schematic diagram showing another sequence of waveforms depicting the effect of changing memory address offset in the differentiating mode.

FIG. 1C shows two separate sets of a sequence of four scans across a wide protracted duration defect. The first set shows the effect of shifting memory II addresses with a N = 1 address offset, whereas an N = 2 offset has been used in the second set. Note that increasing the degree of memory address offset in the digital sense is equivalent to increasing the time constant in a differentiation circuit in the analog sense. This is illustrated by the fact that the edge signals of the N = 1 case are much more distinctive than in the N = 2 offset case. The significance of being able to change N offset value in this invention is to adjust streak detection sensitivity according to the anticipated low frequency content of the protracted duration defect signal, where a large N address offset would correspond to the low frequency class defect (i.e., diffuse edged and wide width class).

We have found that low frequency bias level fluctuations are effectively nulled using this differentiating method, whereas if the straight accumulation method were used, these would soon build up to the point where the bias level change could be discriminated as a protracted duration defect.

The following set of equations define the operation of loop 2 in processing the instantaneous difference signals in differentiating mode 2:

1) $M_{N+S}^{t+1} = M_{N+S}^{t} - D_{N+S}^{t}$

2) $M_{N+S}^{t+2} = M_{N+S}^{t+1} + D_{N}^{t+1}$ $= M_{N+S}^{t} - D_{N+S}^{t} + D_{N}^{t+1}$

3) $M_{N+S}^{t+3} = M_{N+S}^{t+2} - D_{N+S}^{t+2}$ $= M_{N+S}^{t} - D_{N+S}^{t} + D_{N}^{t+1} - D_{N+S}^{t+2}$

4) $M_{N+S}^{t+4} = M_{N+S}^{t+3} + D_{N}^{t+3}$ $= M_{N+S}^{t} - D_{N+S}^{t} + D_{N}^{t+1} - D_{N+S}^{t+2} + D_{N}^{t+3}$ $= M_{N+S}^{t} + (D_{N}^{t+1} + D_{N}^{t+3}) - (D_{N+S}^{t} + D_{N+S}^{t+2})$ where:

$M_N^j$ is the contents of memory in location N during scan j, $D_N^j$ is the value of the instantaneous difference signal loaded in memory address location N during scan j, N, j can be either even or odd integers, and S is the extent of shift.

By examination it can be seen that in those cases where $M_{N+S}^j$ is small, the bias level of the accumulated difference signal will fluctuate about the zero volt level but will permit the defect-related signal to build in two different directions at two distinct locations in memory. Consequently, in the presence of small unidirectional bias level accumulations, either one or the other of the two defect-related signal build-up portions can then be detected by bipolar discrimination means. (For example, the defect signal accumulation over a series of scans shown in FIG. 3, waveform DD).

Such bipolar discrimination means 36 (FIG. 1) is provided to detect the accumulation of protracted duration signals in memory II 22, after these have been converted to analog form by D/A converter 35. The discrimination threshold levels set 40 are dependent on the number (P) of mode 2 scans which the operator selects for adequate product protracted duration defect definition. A streak defect alarm is then effectuated based on bipolar discriminator 36 output signals.

In order to coordinate the operation of the elements of the two loops, the system timing and addressing circuit (STAC) 7 uses a variety of input signals to effect the necessary system control signals shown in FIG. 1A.

An external digital clock 41 produces pulses which are gated by product gate signal 42 which limits all timing events to counts that occur within the product portion of each scan. A counter (not shown) receives the clock pulses and addresses both memories I and II on address line 11. An end of scan signal 43, which may be obtained from a photocell positioned at the end of the scan path as the scanning beam passes over it, is used to reset the memory I, II address counter at the end of each scan. At the same time, end of scan signal 43 is used to step two other counters (not shown), each operating with separate comparator means, also not shown, to produce all mode 1 and 2 control signals in the following manner.

The first comparator is preset with one of three choices (128, 64, 32) for the number of scans needed for calibrating the system in mode 1, by means of $S^n$ set control 44. In addition this counter-comparator combination produces the requisite control signals $C_1$ and $C_2$, 14 and 3, respectively, for loop 1 mode 1 control, and memory I and II write signals 5, 30 respectively. Since the reference values stored in memory I at the end of mode 1 operation can remain fixed indefinitely, a RECAL control 45 is provided to allow the operator to reset the mode 1 counter and thus recalibrate the system, normally at the start of each product run.

The second comparator is preset with the number P scans needed for instantaneous difference signal accumulation in memory II, 22 during mode 2 operation by means of P set control 46 and automatically produces a memory II reset signal 26 at the end of each preselected P scan period. Memory II manual reset control 47 is provided to allow the operator to bypass this automatic feature when protracted duration defects occur in order to clean the slate for the next series of P scans.

Finally, differentiating mode control signal 34 is used to activate a divide by two flip flop (not shown) which is toggled by each end of the scan signal such that, on alternate scans, the values of binary control signals $C_3$ and $C_4$, 23 and 24, change accordingly to effect the differentiating mode signal inversion and memory address location shifts hereinabove described.

Figure 2:
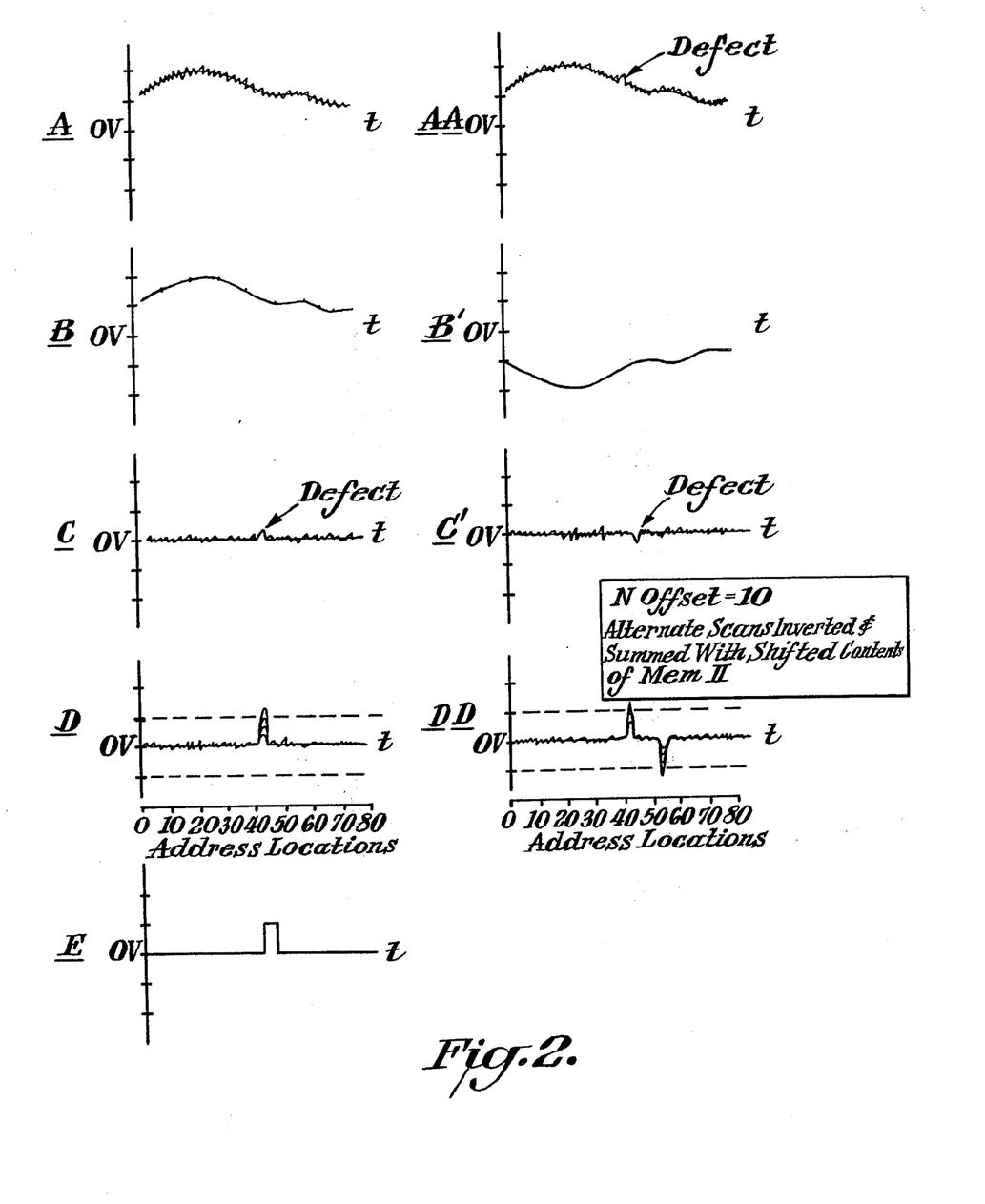
FIG. 2 is a schematic diagram showing a series of waveforms which are typical of those found at the labeled points in FIG. 1 and depicts the operation of the system when low frequency machine direction noise is not present.

To summarize the operation of the pedestal equalizer-streak detector system, refer to FIG. 1 and the waveforms drawn in FIG. 2, which illustrates the system operation at respective points in FIG. 1. FIG. 2 not only depicts the case of detecting narrow streaks when low frequency machine direction noise is not present, but shows both the differentiating mode 2 operation and the standard accumulating method for detecting the subtle protracted duration class defect.

At the outset of calibrating mode 1, 1/0/T/C element 4 furnishes zeros to adder 2 which thereupon sums these to the sampled amplitude values of the first scan log processed signal waveform A to initialize the contents of memory I, 6. Upon the outset of the second scan, 1/0/T/C element 4 allows the contents of memory I, 6 to pass to adder 2 which again sums the corresponding amplitude values of input waveform A to the stored values from memory I. This action continues until a preselected series of $2^n$ scans have occurred and the accumulated partial sum values within each sampling interval are stored in memory I, 6. At this point in time, mode 2 is initiated and a series of events occur: (1) memory I write signal 5 goes low to hold the contents of memory unchanged; (2) divider 13 right justifies the accumulated sums in memory I n places in accordance with the value of $S^n$ signal 5 to produce the best average reference waveform B; (3) 1/0/T/C element 4 passes inverted reference waveform B' and furnishes a binary 1 signal to adder 2 to change the sum values to two's complement form; (4) adder 2 sums the instantaneous amplitude sampled values of waveform AA, a specific scan signal, with the corresponding inverted reference waveform B' samples to produce instantaneous difference signal waveform C; (5) memory II write signal 30 goes high to activate memory II, 22; (6) memory II reset signal 26 causes latch 25 to furnish zeros to adder 21 so that the first instantaneous difference signal can be used to initialize the contents of memory II, 22; and (7) 1/0/T/C element 31 furnishes zeros to adder 33 in order for memory II, 22 to load difference signal data at unshifted address locations.

For the second and succeeding scans in the mode 2 streak detector operations in the non-differentiating mode, those portions of the instantaneous difference signal which do not average out to zero amplitude value over the scan sequence will continue to build-up such as shown in waveform D. Since accumulated signal build-up may occur in either positive or negative directions relating to either heavy or light density regions in the product, a bipolar discriminator is best used to detect either of these occurrences.

In the differentiating mode, control signals $C_3$ and $C_4$ 23, 24 respectively, to 1/0/T/C element 31 cause this element to enter a predetermined address offset into adder 33 on alternate scans so that memory II, 22 will accumulate a persistent signal in the machine direction in two different addressed locations in memory. At the same time that the memory II address locations are shifted on alternate scans, T/C element 20 inverts instantaneous waveform C to produce waveform C'. As adder 21 sums the inverted difference signal waveform C' with the shifted contents of memory on alternate scans, not only will the Gaussian noise amplitude levels be limited but the low frequency signal level shift will be nullified and the bidirectional defect related portions such as shown in FIG. 2, waveform DD, will continue to build.

It is immediately apparent that only four scans are needed for the instantaneous difference signals to build to the point where the streak signal shown in waveform D will be detected to produce defect signal waveform E in the nondifferentiating mode, whereas eight scans are needed in the differentiating mode shown in waveform DD. However, the additional low frequency machine direction noise compensation gained by using this method more than offsets the loss in system sensitivity to the protracted duration class of defect. This is more easily visualized by reference to FIG. 3.

Figure 3:
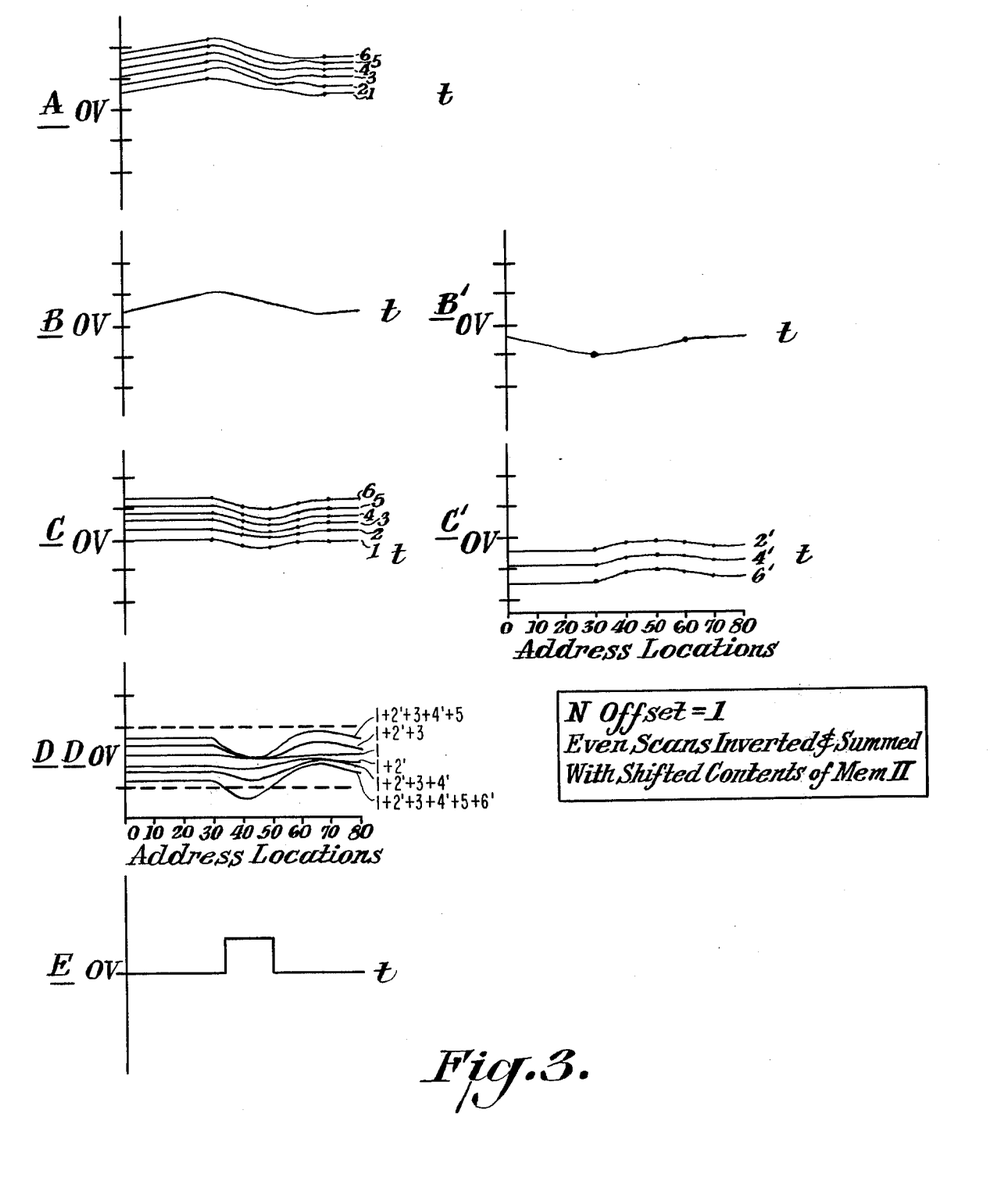
FIG. 3 is a schematic diagram showing an equivalent series of waveforms as shown in FIG. 2 which depicts the operation of the system when low frequency machine direction noise is present.

FIG. 3 is similar to FIG. 2, in that it shows the waveforms appearing at the same points as used for FIG. 2, but in FIG. 3 low frequency machine direction noise is present. An examination of the waveforms will show how this particular influence on the detection of subtle streak conditions can be essentially eliminated by using the differentiating mode. Waveform A shows the slowly increasing signal level of the input signal over a series of six scans. Waveform B shows the results of averaging these scans to obtain a best average reference signal. Waveform B' shows the inverted reference signal. Waveform C shows the resulting series of equalized instantaneous difference signals showing a steadily increasing signal level. Waveform C' shows the inverted even numbered scans which when added to the shifted contents of memory II, 22 produce the bipolar type signal accumulation shown in waveform DD. Note that on the sixth scan, the streak related portion of the accumulated signal has exceeded the negative threshold set into bipolar discriminator 36 to yield a defect indication, waveform E. One can also visualize, by referring to waveform C, that had the straight accumulation technique been used, the accumulation of defect-free portions of the scan in memory II would, on the third scan, exceed the positive threshold regardless of the existence of a protracted duration defect on the scan sequence.

What is claimed is:

1. The method of defect identification with normalizing of the optical-electrical inspection system gain function of scans across a full width of a running product web comprising: (1) storing an accumulation of characteristic individual electrical recurring scan signals A and dividing by the number of said scan signals A accumulated to obtain a reference signal R and (2) differencing each succeeding scan signal A with said stored reference signal R to obtain a zero-based difference signal, thereby equalizing each successive signal a while preserving defect-related signals, and then identifying said defect-related signals by amplitude discrimination of said zero-based difference signal.

2. The method of claim 1 wherein said identification of said defect-related signals is enhanced by coherent adding of said difference signals for a plurality of said scans.

3. The method of claim 2 wherein said difference signals are accumulated over several scans in an order such that the instantaneous difference signal waveforms for alternate scans are inverted and combined with shifted partial sum values of said accumulated difference signals, thereby effectively nullifying the accumulation of periodic bias level changes.

4. Apparatus for defect identification with normalizing of the optical-electrical inspection system gain function of scans across a full width of a running product web comprising, in electrical circuit in the sequence recited, a source of electrical scan signals A, a memory storing a sufficient accumulation of a number of said signals A to permit the resolution of an acceptable average reference signal R, means computing said average signal R as the quotient of said accumulation of said number of said signals A divided by said number of said signals A accumulated, means computing the difference signal A-R for succeeding scan signals A, thereby effectively equalizing each successive scan signal A while preserving defect-related signals, and means identifying said defect-related signals by amplitude discrimination of said difference signal A-R.

5. Apparatus according to claim 4 provided with means for coherent adding of the difference signals A-R for a plurality of said scans.

6. Apparatus according to claim 5 provided with a second memory means for accumulation of said difference signals A-R over several scans, means for shifting the address locations of the partial sum values stored in said second memory means a preselected number of units on successive even (or odd) scans, means for inverting instantaneous difference signals A-R on said even (or odd) scans and means combining said inverted instantaneous difference signals A-R with said stored partial sum values of said accumulation of said difference signals over several scans, thereby effectively nullifying the accumulation of periodic bias level changes.

7. The method of defect identification with normalizing of the optical-electrical system gain function of scans across a full width of a running product web comprising: (1) storing an accumulation of logarithmically processed characteristic individual electrical recurring scan signals A from said system and dividing by the number of said recurring scan signals A accumulated to obtain a reference signal R and (2) differencing each succeeding logarithmically processed scan signal A with said stored reference signal R to obtain the logarithmic ratio signal A/R, thereby equalizing each successive scan signal A while preserving defect-related signals in true perspective to the non-defect containing portions of said signal A/R, and then identifying said defect-related signals by amplitude discrimination of said logarithmic ratio signal A/R.

8. The method of claim 7 wherein said identification of said defect-related signals is enhanced by coherent adding of said logarithmic ratio signals A/R for a plurality of said scans.

9. The method of claim 7 wherein said logarithmic ratio signals A/R are accumulated over several scans in an order such that the instantaneous logarithmic ratio signal waveforms for alternate scans are inverted and combined with shifted partial sum values of said accumulated logarithmic ratio signals A/R, thereby effectively nullifying the accumulation of periodic bias level changes.

10. Apparatus for defect identification with normalizing of the optical-electrical inspection system gain function of scans across a full width of a running product web comprising, in electrical circuit in the sequence recited, an Analog/Digital converter to which logarithmically processed electrical scan signals A are input, a memory storing a sufficient accumulation of a number of said scan signals A to permit the resolution of an acceptable average reference signal R, means computing said average signal R as the quotient of said accumulation of said number of said scan signals A divided by said number of said scan signals A accumulated, means computing the logarithmic ratio signal A/R for each successive scan signal A, by subtraction of the logarithms of signals A and R, thereby effectively equalizing each successive scan signal A while preserving defect-related signals in true perspective to the non-defect containing portions of said signal A/R, and means identifying said defect-related signals by amplitude discrimination of said logarithmic ratio signal A/R.

11. Apparatus according to claim 10 provided with means for coherent adding of the logarithmic ratio signals for a plurality of said scans.

12. Apparatus according to claim 11 provided with a second memory means for accumulation of said logarithmic ratio signals A/R over several scans, means for shifting the address locations of the partial sum values stored in said second memory means a preselected number of units on successive even (or odd) scans, means for inverting instantaneous logarithmic ratio signals A/R on said even (or odd) scans and means combining said inverted instantaneous logarithmic ratio signals A/R with said stored partial sum values of said accumulation of said logarithmic ratio signals A/R over several scans, thereby effectively nullifying the accumulation of periodic bias level changes.

* * * * *